(12) United States Patent
Masters et al.

(10) Patent No.: US 12,622,670 B2
(45) Date of Patent: May 12, 2026

(54) INTEGRATED CARDIAC MAPPING AND PIEZOELECTRIC MICROMACHINED ULTRASONIC TRANSDUCER (pMUT) ULTRASONIC IMAGING CATHETER SYSTEM AND METHOD

(71) Applicant: Boston Scientific Scimed, Inc., Maple Grove, MN (US)

(72) Inventors: Donald Masters, Sylmar, CA (US); Jesus Andres Lopez, Bloomington, CA (US); Eric Stoppenhagen, Santa Monica, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/166,045

(22) Filed: Feb. 8, 2023

(65) Prior Publication Data

US 2024/0260932 A1 Aug. 8, 2024

(51) Int. Cl.
| | |
|---|---|
| *A61B 8/12* | (2006.01) |
| *A61B 8/00* | (2006.01) |
| A61B 8/08 | (2006.01) |

(52) U.S. Cl.
CPC ................. *A61B 8/12* (2013.01); *A61B 8/445* (2013.01); *A61B 8/0883* (2013.01)

(58) Field of Classification Search
CPC .......... A61B 8/12; A61B 8/445; A61B 8/0883
See application file for complete search history.

(56) References Cited

U.S. PATENT DOCUMENTS

| | | | | |
|---|---|---|---|---|
| 5,628,313 | A * | 5/1997 | Webster, Jr. ......... | A61B 5/6858 |
| | | | | 600/374 |
| 5,870,351 | A | 2/1999 | Ladabaum et al. | |
| 5,954,654 | A | 9/1999 | Eaton et al. | |
| 6,277,077 | B1 | 8/2001 | Brisken et al. | |
| 6,547,788 | B1 | 4/2003 | Maguire et al. | |
| 9,454,954 | B2 * | 9/2016 | Hajati .................. | G10K 11/343 |
| 10,932,723 | B2 | 3/2021 | Eliason et al. | |

(Continued)

FOREIGN PATENT DOCUMENTS

| | | |
|---|---|---|
| WO | 2009/073753 A1 | 6/2009 |
| WO | 2023/091769 A1 | 5/2023 |

OTHER PUBLICATIONS

Piezoelectric Micromachined Ultrasonic Transducers (PMUT) (Year: 2024).*

(Continued)

*Primary Examiner* — Brooke Lyn Klein
(74) *Attorney, Agent, or Firm* — Nelson Mullins Riley & Scarborough LLP

(57) ABSTRACT
An integrated cardiac mapping and Piezoelectric Micromachined Ultrasonic Transducer (pMUT) ultrasonic imaging system, is disclosed. The system comprising a pMUT imaging and mapping catheter having a longitudinal axis, a proximal end, and a distal end. A micro-electromechanical (MEMS) based pMUT or other transducer disposed within the distal end of the pMUT imaging and mapping catheter. A pMUT mapping array disposed within the distal end of the pMUT imaging and mapping catheter, wherein the mapping array comprises an expandable basket, grid, hoop, or other configuration with an electronic sensor array arranged on electronic flex circuits.

11 Claims, 10 Drawing Sheets

(56) References Cited

U.S. PATENT DOCUMENTS

| | | | |
|---|---|---|---|
| 11,129,586 | B1 | 9/2021 | Moore et al. |
| 2001/0047134 | A1 | 11/2001 | Holdaway et al. |
| 2003/0199767 | A1* | 10/2003 | Cespedes ................ A61B 5/01 |
| | | | 600/473 |
| 2006/0083772 | A1 | 4/2006 | Dewitt et al. |
| 2006/0235304 | A1 | 10/2006 | Harhen et al. |
| 2007/0038111 | A1 | 2/2007 | Rehrig et al. |
| 2007/0083194 | A1 | 4/2007 | Kunis et al. |
| 2007/0167764 | A1 | 7/2007 | Hynynen |
| 2007/0185397 | A1 | 8/2007 | Govari et al. |
| 2008/0091104 | A1 | 4/2008 | Abraham |
| 2008/0208121 | A1 | 8/2008 | Youssef et al. |
| 2009/0024040 | A1* | 1/2009 | Cespedes ............ A61B 5/0075 |
| | | | 600/467 |
| 2009/0088648 | A1 | 4/2009 | Jaffe et al. |
| 2010/0152590 | A1 | 6/2010 | Moore et al. |
| 2010/0168569 | A1 | 7/2010 | Sliwa et al. |
| 2010/0168583 | A1 | 7/2010 | Dausch et al. |
| 2010/0179424 | A1 | 7/2010 | Warnking et al. |
| 2010/0305451 | A1 | 12/2010 | Kim et al. |
| 2011/0015533 | A1 | 1/2011 | Cox et al. |
| 2011/0028848 | A1 | 2/2011 | Shaquer et al. |
| 2011/0257523 | A1 | 10/2011 | Hastings et al. |
| 2012/0089028 | A1 | 4/2012 | Hadani et al. |
| 2012/0253296 | A1 | 10/2012 | Amano et al. |
| 2013/0053694 | A1 | 2/2013 | Roschak et al. |
| 2013/0231735 | A1 | 9/2013 | Deem et al. |
| 2013/0261467 | A1 | 10/2013 | Dausch et al. |
| 2013/0267853 | A1 | 10/2013 | Dausch et al. |
| 2013/0293065 | A1 | 11/2013 | Hajati et al. |
| 2013/0294202 | A1 | 11/2013 | Hajati |
| 2013/0303919 | A1 | 11/2013 | Corl |
| 2014/0117812 | A1 | 5/2014 | Hajati |
| 2014/0188103 | A1 | 7/2014 | Millett |
| 2014/0236017 | A1 | 8/2014 | Degertekin et al. |
| 2014/0276084 | A1* | 9/2014 | Kemp ...................... A61B 8/12 |
| | | | 600/467 |
| 2014/0276087 | A1 | 9/2014 | Corl |
| 2015/0150497 | A1 | 6/2015 | Goldchmit |
| 2015/0223757 | A1 | 8/2015 | Werneth et al. |
| 2015/0265245 | A1 | 9/2015 | Von Ramm et al. |
| 2015/0305708 | A1 | 10/2015 | Stigall et al. |
| 2015/0366508 | A1* | 12/2015 | Chou ...................... A61N 1/056 |
| | | | 600/467 |
| 2016/0029999 | A1 | 2/2016 | Corl |
| 2016/0113633 | A1 | 4/2016 | Hadjicostis |
| 2016/0199030 | A1 | 7/2016 | Patil et al. |
| 2017/0209121 | A1 | 7/2017 | Davis et al. |
| 2017/0252777 | A1 | 9/2017 | Kidwell et al. |
| 2017/0290562 | A1 | 10/2017 | Corl |
| 2018/0055477 | A1 | 3/2018 | Eskuri |
| 2018/0064415 | A1 | 3/2018 | Zhai et al. |
| 2018/0140278 | A1 | 5/2018 | Bromberg et al. |
| 2018/0146948 | A1* | 5/2018 | Chou .................... A61B 8/466 |
| 2018/0206819 | A1 | 7/2018 | Saarinen et al. |
| 2018/0344283 | A1 | 12/2018 | Rice et al. |
| 2019/0053783 | A1 | 2/2019 | Stigall et al. |
| 2019/0069901 | A1 | 3/2019 | Forbes |
| 2019/0105520 | A1 | 4/2019 | Sverdlik et al. |
| 2019/0357879 | A1 | 11/2019 | Corl |
| 2019/0374196 | A1 | 12/2019 | Courtney et al. |
| 2020/0017906 | A1 | 1/2020 | Lin et al. |
| 2020/0061340 | A1 | 2/2020 | Mixter et al. |
| 2020/0155217 | A1 | 5/2020 | Morneau et al. |
| 2020/0178788 | A1 | 6/2020 | Waters et al. |
| 2020/0245977 | A1 | 8/2020 | Hancock et al. |
| 2020/0330072 | A1 | 10/2020 | Jacobs et al. |
| 2021/0000423 | A1 | 1/2021 | Werneth et al. |
| 2021/0007711 | A1 | 1/2021 | Van et al. |
| 2021/0030394 | A1 | 2/2021 | Caswell et al. |
| 2021/0128106 | A1 | 5/2021 | Salehi et al. |
| 2022/0048071 | A1 | 2/2022 | Sudol |
| 2022/0168545 | A1 | 6/2022 | Lopez et al. |
| 2022/0225960 | A1 | 7/2022 | Cuscuna et al. |
| 2022/0346750 | A1 | 11/2022 | Robinson et al. |
| 2022/0395255 | A1 | 12/2022 | Ryan et al. |
| 2022/0401070 | A1 | 12/2022 | Schaer et al. |
| 2023/0025475 | A1 | 1/2023 | Graham et al. |
| 2023/0165559 | A1 | 6/2023 | Sutherland et al. |
| 2023/0377219 | A1 | 11/2023 | Hennersperger et al. |
| 2024/0023933 | A1 | 1/2024 | Masters et al. |
| 2024/0130707 | A1 | 4/2024 | Masters et al. |

OTHER PUBLICATIONS

Written Opinion and International Search Report issued in PCT/US2024/011842, issued May 17, 2024, 9 pages.

International Preliminary Report on Patentability received for PCT Patent Application No. PCT/US24/11835, mailed on Aug. 28, 2025, 12 pages.

International Preliminary Report on Patentability received for PCT Patent Application No. PCT/US24/11851, mailed on Aug. 28, 2025, 9 pages.

International Search Report and Written Opinion for PCT Application No. PCT/US2023/082324 mailed Jan. 21, 2025. 16 pages.

International Search Report and Written Opinion issued in PCT/US2023/0080430, mailed Apr. 11, 2024.

International Search Report and Written Opinion issued in PCT/US2024/011835, issued Jul. 9, 2024.

International Search Report and Written Opinion issued in PCT/US2024/016370, mailed Jul. 18, 2024.

International Search Report and Written Opinion issued PCT/US2024/011851, issued on May 17, 2024.

International Search Report and Written Opinion received for PCT Patent Application No. PCT/US23/78696, mailed on Mar. 4, 2024, 6 pages.

Richardson et al., "Physiological Implications of Myocardial Scar Structure", 2015, Comprehensive Physiology, vol. 5 Issue 4 (Year: 2015).

Seif et al. "Emergency department diagnosis of infective endocarditis using bedside emergency ultrasound", 2013, Critical Ultrasound Journal, 5:1 (Year: 2013).

* cited by examiner

INTEGRATED CARDIAC MAPPING AND PIEZOELECTRIC MICROMACHINED ULTRASONIC TRANSDUCER (pMUT) ULTRASONIC IMAGING CATHETER SYSTEM AND METHOD

FIELD OF THE DISCLOSURE

The present disclosure relates generally to the field of cardiac mapping and ultrasonic imaging and mapping catheters. More particularly, embodiments relate to mapping catheters having a distal piezoelectric micromachined transducer for transmitting and receiving acoustic pulse information.

BACKGROUND OF THE DISCLOSURE

Use of catheter-based structural and electrophysiological procedures have recently expanded to more complex scenarios, in which an accurate definition of variable individual cardiac anatomy is a key to obtain optimal results. In electrophysiology procedures, piezoelectric micromachined ultrasonic transducer (pMUT) imaging allows integration of real-time images with mapping to guide transcatheter cardiac procedures. Cardiac mapping utilizes electrodes that measure the electrical activity of the cardiac tissue. This is transferred into mapping system software where a 3D model is created of the heart, a color-coded overlay showing the electrical waves generated during each heartbeat, the touch points where the tissue was mapped, and showing the location of the catheter inside the heart. Tissue identified as having unhealthy electrical activity that is cause an arrhythmia can then be ablated directly or isolated using an ablation catheter to cause small burns/scar tissue that block electrical signals. The pMUT imaging integration allows a real-time assessment of cardiac anatomy during interventional procedures and guides catheter manipulation in relation to the different anatomic structures. Therefore, there is a need for an improved mapping catheters that integrate ultrasonic pMUT imaging.

Atrial Fibrillation (AF) is one of the most widespread and sustained cardiac arrhythmias and it affects more than 30 million people worldwide. While prevalence in developed nations tends to be small, nearly 1%-4%. The AF is steadily increasing, and it is well known that the AF is associated with an increased risk of all-cause mortality, heart failure, thromboembolism, and dementia. Catheter mapping is an alternative treatment option that is more effective than antiarrhythmic medications. Pulmonary vein isolation (PVI), which involves electrically isolating the pulmonary veins (PV) from the left atrium, remains the cornerstone of Atrial Fibrillation (AF) mapping. The catheter mapping is necessary to locate triggers and substrate so that an ablation strategy can be optimized. The most used cardiac mapping approach is isochronal or activation mapping, which aims to create a spatial model of electrical wavefront propagation. The catheter mapping increase ability to perform rapid simultaneous contact mapping of the chamber. Typically, modern mapping technologies which may improve the efficacy, safety, and efficiency of mapping for persistent AF. Further, current technology requires the use of a separate mapping, ablation catheter and an Intracardiac Echocardiography (ICE) pMUT imaging catheter. ICE has applications for structural heart pMUT imaging of the left atrial appendage (LAA), to aid in septal defect closures and visualizing the fossa ovalis and plays a role in transcatheter valve replacement. It also is used in EP procedures for ablation catheter guidance. ICE confirms the exact location of the catheter tip to aid with more accurate ablations. ICE also can help with safety monitoring of the pericardial space for tamponade or pericardial effusion caused in rare cases by either the transeptal puncture or the ablation. ICE is expected to become increasingly important to better guide an increasing number of transcatheter ablation procedures. Once transcatheter aortic and mitral valve heart valve replacement and LAA occlusion devices gain U.S. Food and Drug Administration (FDA) clearance, ICE is expected to see increased use for the accurate deployment of these devices.

Further, the AF refers to a type of cardiac arrhythmia where there is disorganized electrical conduction in the atria causing rapid uncoordinated contractions that result in ineffective pumping of blood into the ventricle and a lack of synchrony. During AF, the atrioventricular node receives electrical impulses from numerous locations throughout the atria instead of only from the sinus node. This overwhelms the atrioventricular node into producing an irregular and rapid heartbeat. As a result, blood pools in the atria that increases a risk for blood clot formation. The major risk factors for atrial fibrillation include age, coronary artery disease, rheumatic heart disease, hypertension, diabetes, and thyrotoxicosis. The AF affects 7% of the population over age 65.

Moreover, the AF treatment options are limited. Lifestyle change only assists individuals with lifestyle related AF. Medication therapy assists only in the management of AF symptoms, may present side effects more dangerous than atrial fibrillation, and fail to cure AF. Electrical cardioversion often restores sinus rhythm but has a high recurrence rate. In addition, if there is a blood clot in the atria, cardioversion may cause the clot to leave the heart and travel to the brain or to some other part of the body, which may lead to stroke. Therefore, there is a need for an improved cardiac mapping and pMUT ultrasound imaging catheter system.

SUMMARY OF THE DISCLOSURE

By way of introduction, the preferred embodiments described below include an easy-to-use integrated cardiac mapping and Piezoelectric Micromachined Ultrasonic Transducer (pMUT) ultrasonic imaging catheter system is disclosed. The integrated cardiac mapping and pMUT ultrasonic imaging catheter system comprises a pMUT imaging and mapping catheter having a longitudinal axis, a proximal end, and a distal end. Further, an ultrasonic pMUT transducer array is disposed within the distal end of the pMUT imaging and mapping catheter. The ultrasonic pMUT transducer array comprises a plurality of pMUT transducer array elements arranged on a substrate. It can be noted that the plurality of pMUT transducer array elements corresponds to a micro-electromechanical (MEMS) based pMUT. Further, the integrated cardiac mapping and pMUT ultrasonic imaging catheter system comprises a catheter shaft connected at one end to a handle assembly and at other end to the ultrasonic pMUT transducer array. The catheter shaft encloses an electronic flex cable which is in communication with at least one signal trace and is configured to: direct each of the plurality of pMUT transducer array elements, via the at least one signal trace, to transmit and receive, with respect to heart, ultrasound beams having a bandwidth including a predetermined fundamental mode vibration of each of the plurality of pMUT transducer array elements, such that a single array element can transmit and receive multiple fundamental mode vibrations simultaneously; receive at least one signal from the plurality of pMUT transducer array elements based on transmitting and receiving at least one ultrasound beam of the ultrasound beams, and construct at least one image of at least a portion of the heart based on the at least one signal.

In one embodiment, the integrated cardiac mapping and pMUT ultrasonic imaging catheter system comprises a mapping catheter consisting of an open-lumen catheter shaft with a collapsible, basket-shaped distal end, which is composed of a plurality of electrodes mounted on flexible, self-expanding, equidistant metallic splines electrodes. The mapping catheters are constructed of a flexible material to allow passive deployment of the array catheter and optimize endocardial contact.

According to another aspect of the invention, an integrated ultrasonic imaging and mapping system is disclosed. The integrated ultrasonic imaging and mapping system comprises a mapping catheter having a longitudinal axis, a proximal end, and a distal end. Further, the integrated ultrasonic imaging and mapping system comprises a MEMS based Piezoelectric Micromachined Ultrasonic Transducer (pMUT) array disposed within the distal end of the mapping catheter. The MEMS based pMUT array comprises a substrate and a plurality of MEMS based pMUT array elements arranged on the substrate. Further, the integrated ultrasonic imaging and mapping system comprises a mapping array disposed within the distal end of the mapping catheter, wherein the mapping array comprises an expandable basket, grid, hoop, or other configuration with an electronic sensor array arranged on electronic flex circuits.

According to another aspect of the invention, a medical device is disclosed. The medical device comprises a catheter shaft, a first carrier assembly and a second carrier assembly. The first carrier assembly coupled to the catheter shaft and having a first radially expandable array of electrodes coupled to a plurality of first carrier arms. The second carrier assembly rotatably coupled to the catheter shaft and having a second radially expandable array of electrodes coupled to a plurality of second carrier arms, the second carrier assembly rotatable about the first carrier assembly.

BRIEF DESCRIPTION OF THE DRAWINGS

The accompanying drawings illustrate various embodiments of systems, methods, and embodiments of various aspects of the disclosure. Any person of ordinary skill in the art will appreciate that the illustrated element boundaries (e.g., boxes, groups of boxes, or other shapes) in the figures represent one example of the various boundaries representative of the disclosed invention. It may be that in some examples one element may be designed as multiple elements or that multiple elements may be designed as one element. In other examples, an element shown as an internal component of one element may be implemented as an external component in another and vice versa. Furthermore, elements may not be drawn to scale. Non-limiting and non-exhaustive descriptions of the present disclosure are described with reference to the following drawings. The components in the figures are not necessarily to scale, emphasis instead being placed upon the illustrated principles.

Various embodiments will hereinafter be described in accordance with the appended drawings, which are provided to illustrate and not to limit the scope of the disclosure in any manner, wherein similar designations denote similar elements, and in which.

DETAILED DESCRIPTION

The components of the embodiments as generally described and illustrated in the figures herein can be arranged and designed in a wide variety of different configurations. Thus, the following more detailed description of various embodiments, as represented in the figures, is not intended to limit the scope of the present disclosure but is merely representative of various embodiments. While various aspects of the embodiments are presented in drawings, the drawings are not necessarily drawn to scale unless specifically indicated.

Some embodiments of this disclosure, illustrating all its features, will now be discussed in detail. The words "comprising," "having," "containing," and "including," and other forms thereof, are intended to be equivalent in meaning and be open-ended in that an item or items following any one of these words is not meant to be an exhaustive listing of such item or items or meant to be limited to only the listed item or items.

It must also be noted that as used herein and in the appended claims, the singular forms "a," "an," and "the" include plural references unless the context dictates otherwise. Although any systems and methods similar or equivalent to those described herein can be used in the practice or testing of embodiments of the present disclosure, the preferred systems, and methods are now described. The terms "proximal" and "distal" are opposite directional terms. For example, the distal end of a device or component is the end of the component that is furthest from the practitioner during ordinary use. The proximal end refers to the opposite end, or the end nearest the practitioner during ordinary use.

Embodiments of the present disclosure will be described more fully hereinafter with reference to the accompanying drawings in which like numerals represent like elements throughout the several figures, and in which example embodiments are shown. Embodiments of the present disclosure may, however, be embodied in alternative forms and should not be construed as being limited to the embodiments set forth herein. The examples set forth herein are non-limiting examples and are merely examples among other possible examples.

Figure 1:
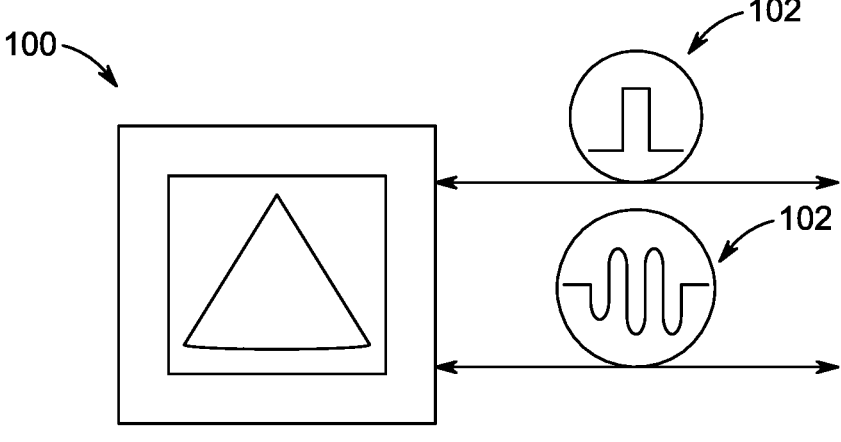
FIGS. 1 and 2 illustrate a prior art imaging system, for acquiring two-dimensional image information.
Figure 2:
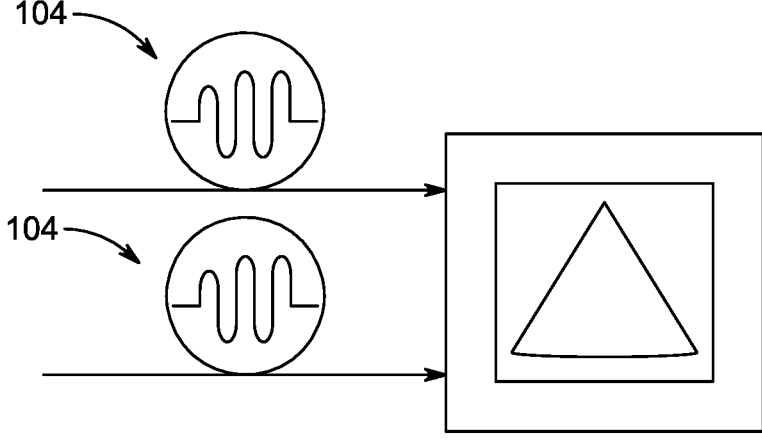

FIGS. 1 and 2 illustrate a prior art imaging system 100. The imaging system 100 provides an ultrasound transmit pulse 102 and an ultrasound receive path 104, for connection to an ultrasonic transducer (not shown). The ultrasound transmit pulse 102 may transmit ultrasound signals from the imaging system 100 towards an object such as heart of a patient. Further, the ultrasound receive path 104 may create a waveform based at least on the ultrasound signals. Thereafter, the imaging system 100 may convert the received ultrasound signals or ultrasound information to a two-dimensional (2D) image of the object or a portion of the object.

Figures 3, 4:
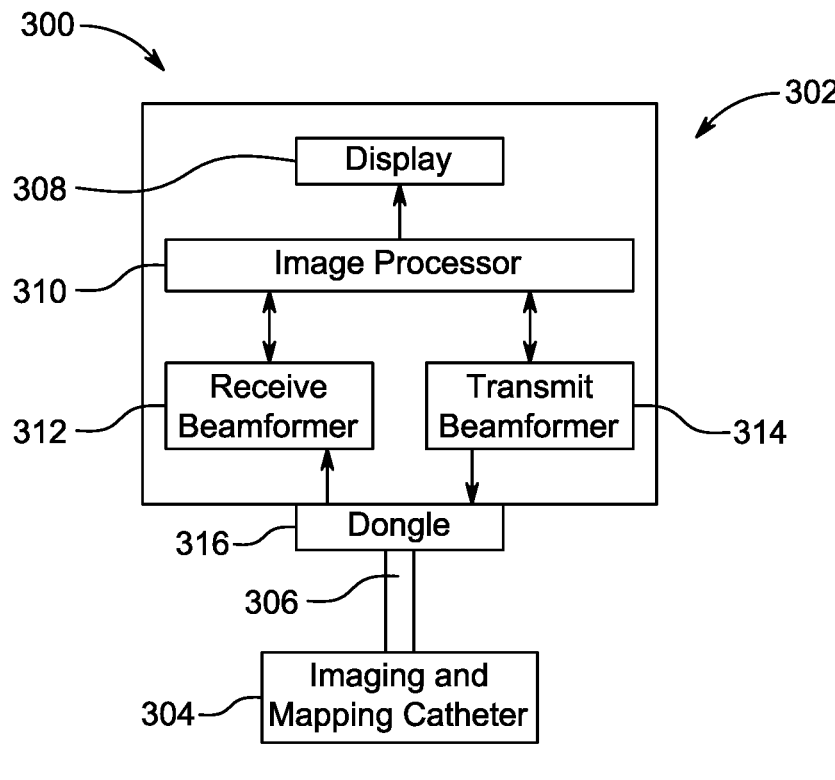
FIG. 3 illustrates a schematic diagram of an integrated cardiac mapping and Piezoelectric Micromachined Ultrasonic Transducer (pMUT) ultrasonic imaging catheter system, according to an embodiment of the present disclosure.
FIG. 4 illustrates a multi-channel electronic communication between a pMUT imaging and mapping device and a pMUT imaging and mapping catheter, according to an embodiment of the present disclosure.

FIG. 3 illustrates a schematic diagram of an integrated cardiac mapping and Piezoelectric Micromachined Ultrasonic Transducer (pMUT) ultrasonic imaging catheter system 300, according to an embodiment of the present disclosure.

In one embodiment, the integrated cardiac mapping and pMUT ultrasonic imaging catheter system 300 may utilize a microelectromechanical (MEMS) pMUT transducer array defined as pMUT or other types of MEMS transducers, interconnected using matched flexible circuits. It can be noted that the use of the high-density flexible circuits may enable highly repeatable and stable transmission and return signals. Further, the high-density flexible circuit transmission lines may transmit electrical energy from one end to another distal end of the integrated cardiac mapping and pMUT ultrasonic imaging catheter system 300.

The integrated cardiac mapping and pMUT ultrasonic imaging catheter system 300 may comprise a pMUT imaging and mapping device 302 linked to a pMUT imaging and mapping catheter 304 via a communication channel 306. The pMUT imaging and mapping device 302 may comprise a display 308, an image processor 310, a receive beamformer 312, a transmit beamformer 314 and a dongle 316. The pMUT imaging and mapping catheter 304 may be disposed within a chamber of a heart of a patient and the pMUT imaging and mapping device 302 may receive at least one signal from the pMUT imaging and mapping catheter 304. The at least one signal may be communicated from the pMUT imaging and mapping catheter 304 to the pMUT imaging and mapping device 302 via an electronic flex cable (not shown) connected to the dongle 316.

The image processor 310 may be configured to generate a two-dimensional (2D) image according to data received from the pMUT imaging and mapping catheter 304. In one embodiment, the image processor 310 may be configured to receive a focused signal from the receive beamformer 312. The image processor 310 may render the data to construct an image or sequence of images. In one embodiment, the image may be three-dimensional (3D) representation, such as a two-dimensional image rendered from a user or a processor selected viewing direction. In one embodiment, the image processor 310 may be a detector, filter, processor, application-specific integrated circuit, field-programmable gate array, digital signal processor, control processor, scan converter, three-dimensional image processor, graphics processing unit, analog circuit, digital circuit, or combinations thereof. The image processor 310 may receive beamformed data and may generate images, to display on the display 308. It can be noted that the generated images are associated with a two-dimensional (2D) scan. Alternatively, the generated images may be three-dimensional (3D) representations.

The image processor 310 may be programmed for hardware accelerated two-dimensional re-constructions. The image processor 310 may store processed data of the at least one signal and a sequence of images in a memory. In one embodiment, the memory may be a non-transitory computer-readable storage media. The instructions for implementing the processes, methods and/or techniques discussed herein are provided on the computer-readable storage media or memories, such as a cache, buffer, RAM, removable media, hard drive, or other computer-readable storage media. Non-transitory computer-readable storage media include various types of volatile and non-volatile storage media. The functions, acts, or tasks illustrated in the figures or described herein are executed in response to one or more sets of instructions stored in or on a computer readable storage media. The functions, acts, or tasks are independent of the particular type of instruction sets, storage media, processor, or processing strategy and may be performed by software, hardware, integrated circuits, firmware, micro code, and the like, operating alone or in combination.

Figure 6:
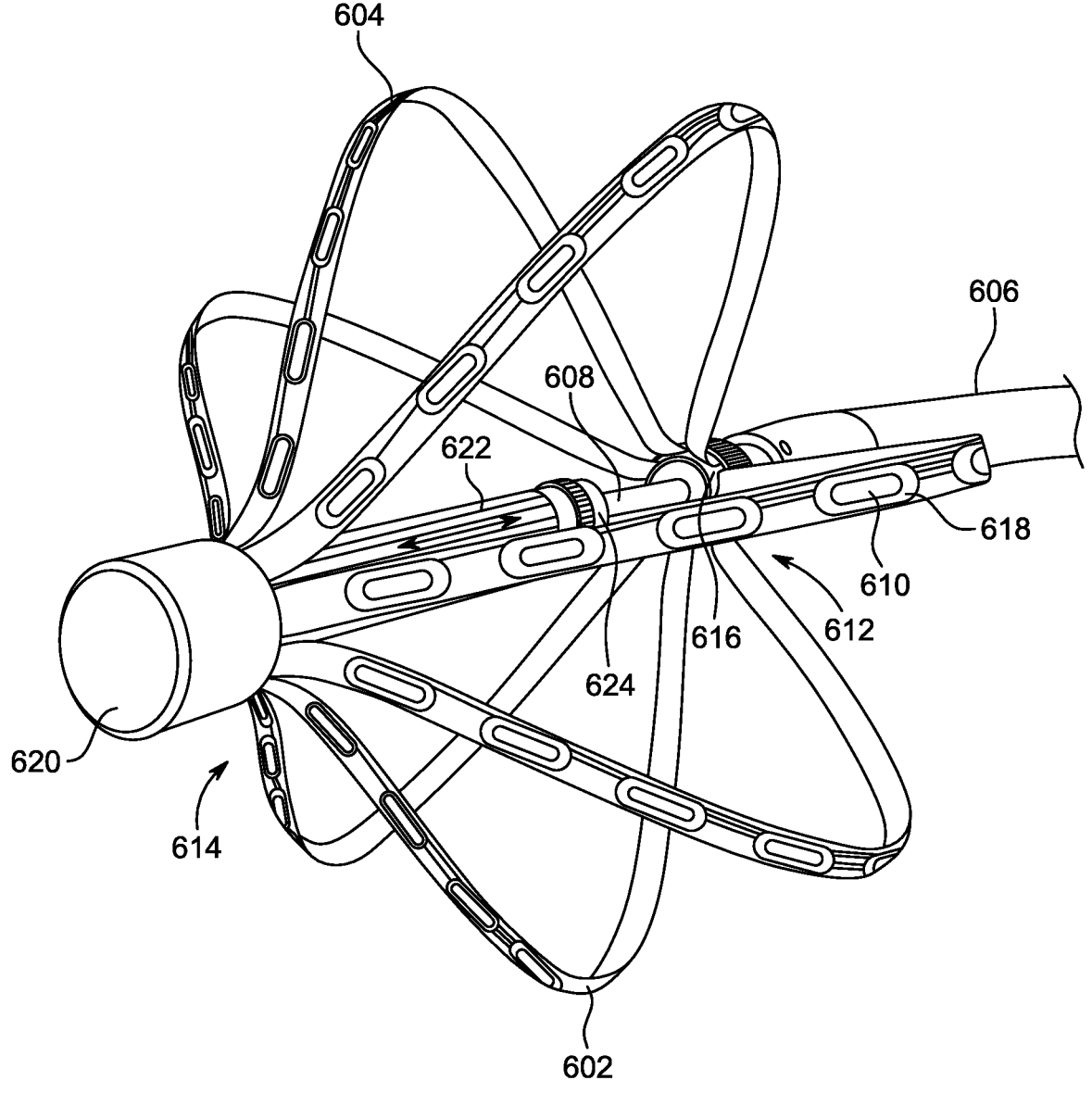
FIG. 6 illustrates a perspective view of the distal portion of the pMUT imaging and mapping catheter, according to an embodiment of the present disclosure.

The pMUT imaging and mapping catheter 304 may be in electronic communication with the pMUT imaging and mapping device 302 for transmission and receiving of ultrasound signals to and from an arterial wall of a vascular system. In one embodiment, the pMUT imaging and mapping catheter 304 may be configured to visualize standard echocardiography views of the heart, such as in a standard version, a right atrium may be visualized. The pMUT imaging and mapping catheter 304 may be employed in transseptal catheterization for several percutaneous interventions, including left heart catheter mapping, atrial septal defect closure for effective alternative to surgical intervention. In one embodiment, the pMUT imaging and mapping catheter 304 may comprise a body having a longitudinal axis, a proximal end, a distal end, a handle assembly, a catheter shaft, an electronic flex cable, and a distal tip, as shown in FIG. 6.

Referring to FIG. 4, a multi-channel electronic communication between the pMUT imaging and mapping device 302 and the pMUT imaging and mapping catheter 304 is disclosed, according to an embodiment of the present disclosure.

The pMUT imaging and mapping catheter 304 may comprise a MEMS based pMUT array 402 coupled to the pMUT imaging and mapping device 302 via the catheter shaft (not shown) and the dongle 316. The dongle 316 may be referred as a communication channel connected to the catheter shaft.

The MEMS based pMUT array 402 may comprise a plurality of pMUT array elements 404 arranged on a substrate 406. Further, each of the plurality of pMUT array elements 404 may provide a wide bandwidth of an individual focused beam. The MEMS based pMUT array 402 may be coupled to the pMUT imaging and mapping device 302 using the dongle 316, as described earlier. The MEMS based pMUT array 402 disposed within the distal end of the pMUT imaging and mapping catheter 304 may transmit the at least one signal via the electronic flex cable inside the catheter shaft to the pMUT imaging and mapping device 302. The at least one signal may be the acoustic echo transmitted from the MEMS based pMUT array 402. It can be noted that the acoustic echo of acoustic energy may be received from a face of the MEMS based pMUT array 402 and received at the image processor 310.

The ultrasound beams may have a bandwidth including a predetermined fundamental mode vibration of each of the plurality of pMUT array elements 404, such that a single array element can transmit and receive multiple fundamental mode vibrations simultaneously. It can be noted that the plurality of pMUT array elements 404 may transmit and receive the ultrasound beams with respect to the heart or at least a portion of the heart. Further, the electronic flex cable inside the catheter shaft may be configured to receive at least one signal from the plurality of pMUT array elements 404 based on transmitting and receiving at least one ultrasound beam of the ultrasound beams. The pMUT imaging and mapping device 302 may be further configured to construct at least one image of at least the portion of the heart based on the at least one signal. It can be noted that the electronic flex cable may be configured to the transmit beamformer 314 and the receive beamformer 312 to display a two-dimensional (2D) image information of the heart or the at least portion of the heart.

In one embodiment, the plurality of pMUT array elements 404 may correspond to MEMS based pMUTs. The catheter shaft may be connected to the handle assembly 324 at one end and to the MEMS based pMUT array 402 at other end. The electronic flex cable inside the catheter shaft may be in communication with the at least one signal trace. It can be noted that the electronic flex cable may be further communicate to the transmit beamformer 314 and the receive beamformer 312, via the dongle 316 to display a two-dimensional (2D) image information of the heart to be scanned.

Figure 5:
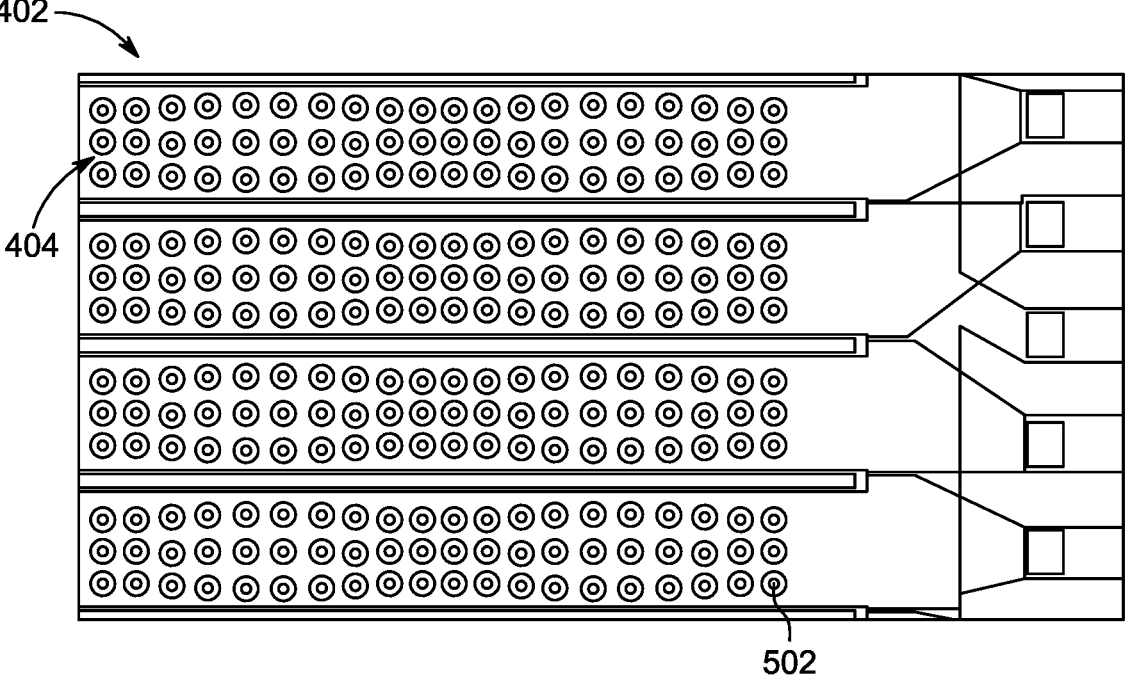
FIG. 5 illustrates a sectional view of a distal end of the pMUT imaging and mapping catheter with a plurality of pMUT transducer array elements, according to an embodiment of the present disclosure.

Referring to FIG. 5, a sectional view of a distal end of the pMUT imaging and mapping catheter 304 with a plurality of pMUT transducer array elements 402 is disclosed, according to an embodiment of the present disclosure.

The MEMS based pMUT array 402 may comprise the plurality of pMUT array elements 404, arranged towards the distal end of the pMUT imaging and mapping catheter 304. The distal end of the pMUT imaging and mapping catheter 304 may be provided with the MEMS based pMUT array 402 having the plurality of pMUT array elements 404. Further, each of the plurality of pMUT array elements 404 may have a plurality of individual transducer cells 502 arranged in a manner to provide a wide bandwidth of the individual focused beam. In one embodiment, the MEMS based pMUT array 402 may be constructed from a pMUT array containing individual elements of different diameters. In one embodiment, to achieve wider bandwidth with pMUT arrays, multiple diameters of pMUT cells may be integrated into one element. It can be noted that by arranging pre-shaped pMUTs with different diameters, a broader bandwidth can be realized through the complex interaction between the individual pMUT elements. In one embodiment, the pMUT cells of multiple diameters may achieve a bandwidth of greater than 55%. For example, in 3 elements, there are 5 different dome diameters, and each array is of a different size, such as 300 μm.

Figure 7:
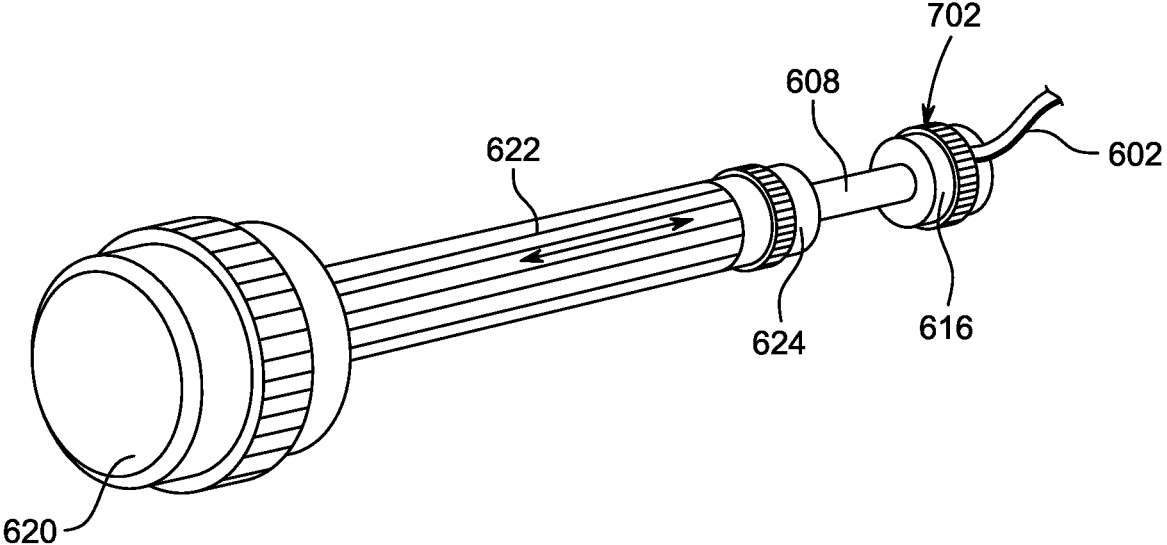
FIG. 7 illustrates a plurality of circular mapping pMUT arrays arranged in a cylindrical fashion, according to an embodiment of the present disclosure.
Figure 8:
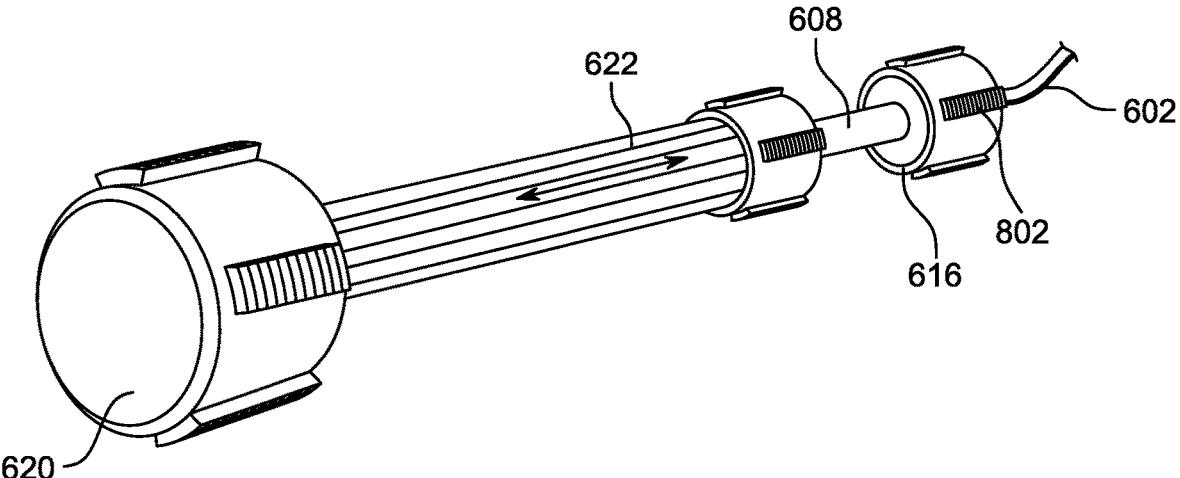
FIG. 8 illustrates a plurality of linear pMUT imaging array arranged in a linear fashion, according to an embodiment of the present disclosure.

Further, the MEMS based pMUT array 402 may correspond to pMUT and the plurality of pMUT array elements 404 may correspond to a plurality of pMUT elements. In one embodiment, the plurality of pMUT elements may be directed to transmit and receive, the ultrasound beams having the bandwidth including the predetermined fundamental mode vibration of each of the plurality of pMUT elements, such that a single pMUT element can transmit and receive multiple fundamental mode vibrations simultaneously. Further, the electronic flex cable inside the catheter shaft receives the at least one signal from the plurality of pMUT elements. It can be noted that the at least one signal may correspond to the at least one ultrasound beam. The at least one signal may be transmitted to the pMUT imaging and mapping device 302 for further processing in the image processor 310. The image processor 310 may construct the at least one image of the heart. It can be noted that the plurality of pMUT elements may be used to create the individual focused beam. In one embodiment the pMUT elements are arranged in a linear fashion. In a second embodiment the pMUT in arranged in cylinder fashion, as shown in FIGS. 7-8.

Referring to FIG. 6, a perspective view of the distal portion of the pMUT imaging and mapping catheter 304 is disclosed, according to an embodiment of the present disclosure, in which the device includes an electronic connection assembly and a distal mapping carrier assembly.

The pMUT imaging and mapping catheter 304 may comprise a plurality of expandable baskets 602 with a plurality of flexible splines 604 disposed alternatively along the length of each of the plurality of expandable baskets 602. The plurality of expandable baskets 602 may be disposed serially along a single axis, in an umbrella tip configuration. Further, the pMUT imaging and mapping catheter 304 includes an elongate tube as a catheter shaft 606, preferably constructed of Pebax material and approximately 6-8 French diameter. Alternatively, instead of expandable baskets, the mapping catheter may comprise of a grid, hoop, or other configuration. The catheter shaft 606 slidingly receives a first control shaft 608. The first control shaft 608 is attached towards a distal portion to the plurality of expandable baskets 602, grid, hoop, or another configuration.

Further, the plurality of flexible splines 604 configured with electronic sensors 610. The plurality of flexible splines 604 may have a first end 612 and a second end 614. The first end 612 of the plurality of flexible splines 604 is attached to a control on the proximal end of the pMUT imaging and mapping catheter 304 configured to allow an operator to precisely advance and retract the plurality of expandable baskets 602, grid, hoop, or another configuration.

Further, the pMUT imaging and mapping catheter 304 may comprise the first carrier assembly (not shown) and the second carrier assembly coupled to the catheter shaft 606. The first carrier assembly and the second carrier assembly may have a first radially expandable array of electrodes and a second radially expandable array of electrodes coupled to a plurality of first carrier arms and a plurality of second carrier arms (not shown). It can be noted that the first and second radially expandable array of electrodes may correspond to the electronic sensors 610. It can also be noted that the plurality of first carrier arms and the plurality of second carrier arms may correspond to the plurality of flexible splines 604. The second carrier assembly is rotatable about the first carrier assembly. In one embodiment, the first and second radially expandable array of electrodes may have a series of longitudinally spaced electrodes or the electronic sensors 610 longitudinally spaced along the plurality of expandable baskets 602. Alternatively, instead of expandable baskets, the mapping catheter may comprise of a grid, hoop, or other configuration.

Further, the pMUT imaging and mapping catheter 304 may comprise a first ring 616 on the first end 612. The first ring 616 fixedly attaches one end of the plurality of flexible splines 604. The plurality of flexible splines 604 may be made from Nitinol. It can be noted that Nitinol is resiliently biased in a straight or umbrella tip configuration. Further, advancement and retraction of the first control shaft 608 changes the diameter of the plurality of expandable baskets 602, including a fully compacted (minimal diameter) radial state when the first control shaft is fully advanced, and a maximum diameter state when first control shaft 608 is fully retracted.

Further, the pMUT imaging and mapping catheter 304 may comprise mapping elements 618 fixedly mounted to each of the plurality of flexible splines 604. The mapping elements 618 are configured to map the pathways in the tissue. Further, the mapping elements 618 may comprise the electronic sensor 610 configured to map. In another embodiment, the mapping elements 618 are attached to wires (not shown) which travel proximally to the proximal end of the pMUT imaging and mapping catheter 304 for attachment to an energy delivery unit, a mapping unit, and/or another electronic device for sending or receiving signals and/or power.

Further, the mapping elements 618 are configured to map electrical activity present in tissue to target areas for creating lesions and/or otherwise assess a patient condition. In one embodiment, the mapping elements 618 are constructed of an electronic sensor, a conductive material, such as platinum or a combination of platinum and iridium. Further, the mapping elements 618 may comprise integral temperature sensors, such as a thermos couple welded to an internal portion of the mapping elements 618. In another embodiment, the mapping elements 618 and integral temperature or other sensors, are attached to wires (not shown) which travel proximally to the proximal portion of the pMUT imaging and mapping catheter 304 for attachment to an pMUT imaging engine, mapping unit, an energy delivery unit, and/or another electronic device for sending or receiving signals and/or power.

Further, the first control shaft 608 comprises a distal tip 620 towards a distal end. In one embodiment, the distal tip 620 may be preferably constructed of a soft or flexible material, such as, a soft plastic or an elastomer which is atraumatic to tissue and is preferably radiopaque, such as a Pebax material doped with Barium Sulfate. It can be noted that the distal tip 620 is constructed to help navigation into and stabilization within a pulmonary vein. Further, the first control shaft 608 may comprise a cylindrical section 622 between the first ring 616 and the distal tip 620. Further the cylindrical section 622 is configured to move on the first control shaft 608. Further, the cylindrical section 622 is configured to move the first ring 616 in a forward and a backward direction, to expand or retract the plurality of expandable baskets 602, grid, hoop, or other configuration for mapping heart walls. Further, the first ring 616 may be mounted with MEMS based pMUT transducers configured to image the heart walls, as shown in FIGS. 7-8.

Further, the pMUT imaging and mapping catheter 304 may comprise a second ring 624 between the first end 612 and the second end 614 proximal to the cylindrical section 622. In one embodiment, the cylindrical section 622 may correspond to a cylinder in a radial motion between the first end 612 and the second end 614. The second ring 624 may be positioned over the first control shaft 608. Further, the first ring 616 and the second ring 624 may be mounted with the MEMS based pMUT array 402 in a circular or cylindrical fashion, as shown in FIGS. 7-8.

FIG. 7 illustrates a plurality of circular mapping pMUT arrays 702 arranged in a cylindrical fashion, according to an embodiment of the present disclosure.

In one embodiment, the first ring 616, the distal tip 620 and the second ring 624 may be mounted with the plurality of circular mapping pMUT arrays 702 arranged in a cylindrical fashion. In one embodiment, the plurality of circular mapping pMUT arrays 702 correspond to a pMUT circular array or pMUT elements.

FIG. 8 illustrates a plurality of linear pMUT imaging array 802 arranged in a linear fashion, according to an embodiment of the present disclosure.

In one embodiment, the first ring 616, the distal tip 620 and the second ring 624 may be mounted with the plurality of linear pMUT imaging arrays 802 arranged in linear fashion.

In one embodiment, the plurality of circular mapping pMUT arrays 702 and the plurality of linear pMUT imaging array 802 may be arrays of mapping elements, preferably geometrically adjustable electrode arrays, and may be configured in a wide variety of ways and patterns. In another embodiment, the plurality of circular mapping pMUT arrays 702 and the plurality of linear pMUT imaging array 802 provide electrical energy, such as radiofrequency (RF) energy, in monopolar (unipolar), bipolar or combined monopolar-bipolar fashion, as well as methods for treating conditions (e.g., atrial fibrillation, supra ventricular tachycardia, atrial tachycardia, ventricular tachycardia, ventricular fibrillation, and the like). Further, multiple types of mapping catheters may be employed for different minimally invasive procedures, such as, atrioventricular (AV) node ablation which is a treatment for an irregularly fast and disorganized heartbeat called atrial fibrillation, cryoablation in which an extremely cold liquid or an instrument called a cryoprobe is used to freeze and eliminate abnormal tissue, and an epicardial ablation in which a regular heart rhythm is restored, by creating tiny scars on outside of the heart to block faulty electrical signals that cause the heart to beat too fast.

Figure 9:
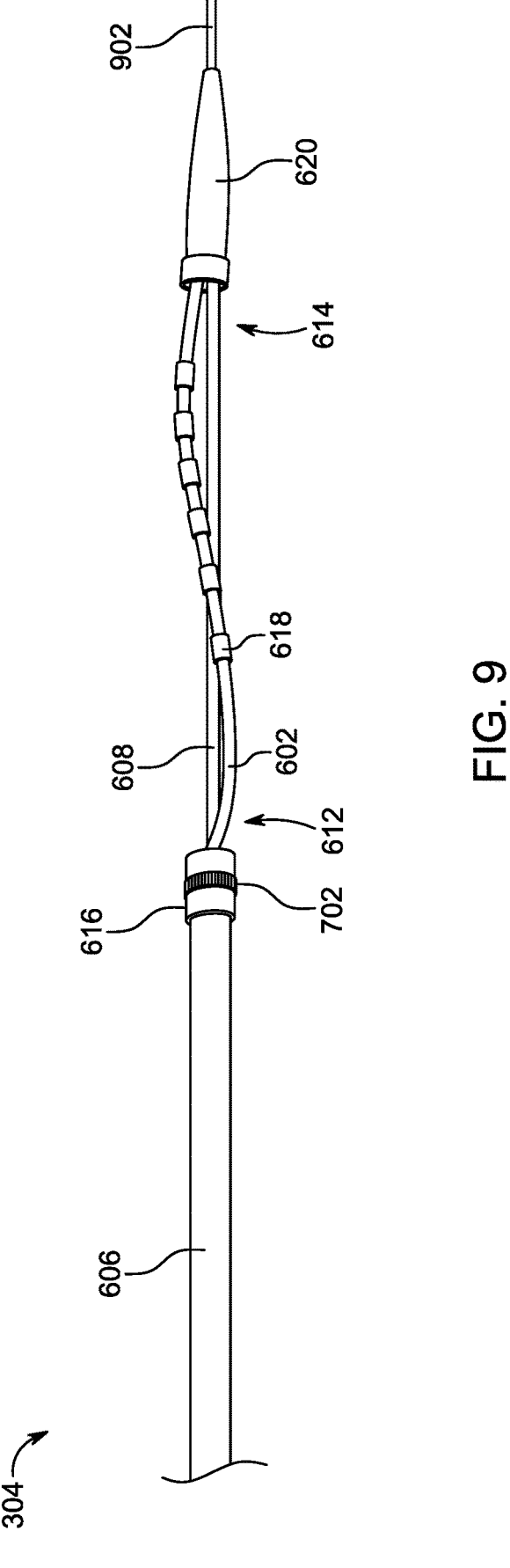
FIG. 9 illustrates a perspective view of a distal portion of the pMUT imaging and mapping catheter in a partially deployed state, with the plurality of circular pMUT imaging arrays arranged in a linear fashion, according to an embodiment of the present disclosure.

Referring to FIG. 9, a perspective view of a distal portion of an alternate pMUT imaging and mapping catheter 304 in a partially deployed state, with the plurality of circular pMUT imaging arrays 702 arranged in a linear fashion, is disclosed, according to an embodiment.

The first control shaft 608 of the pMUT imaging and mapping catheter 304 is in linear configuration for advancing the pMUT imaging and mapping catheter 304 over a guidewire 902. The guidewire 902 may be advanced for an intraluminal advancement when inserted into a femoral vein, and travels to the heart, through the septum separating the right atrium and left atrium (e.g., through a transeptal sheath), and into a pulmonary vein such as the left superior pulmonary vein. The first control shaft 608 is placed in this linear, maximally compact configuration by advancing first control shaft 608, such as by manipulating a control on a handle. The plurality of expandable baskets 602, grid, hoop, or other configuration comprises the mapping elements 618. The plurality of expandable baskets 602 or alternative configuration has a proximal end fixedly attached to the catheter shaft 606 via the first ring 616. It can be noted that the first ring 616 may also be referred as a crimp ring. The plurality of circular pMUT imaging arrays 702 are arranged over the first ring in the linear fashion. The first end 612 of plurality of flexible splines 604 is fixedly attached to the first control shaft 608 at a radial location of 90° offset from proximal end attachment, such that the plurality of flexible splines 604 radially expands as the first control shaft 608 is retracted. The distal end of the first control shaft 608 is covered with the distal tip 620. The cylindrical section 622 is slidably positioned up against the distal tip 620. In one embodiment, the distal tip 620 may be an atraumatic tip with an exit hole (not shown) in communication with the internal guidewire lumen through which guidewire passes.

Figure 10:
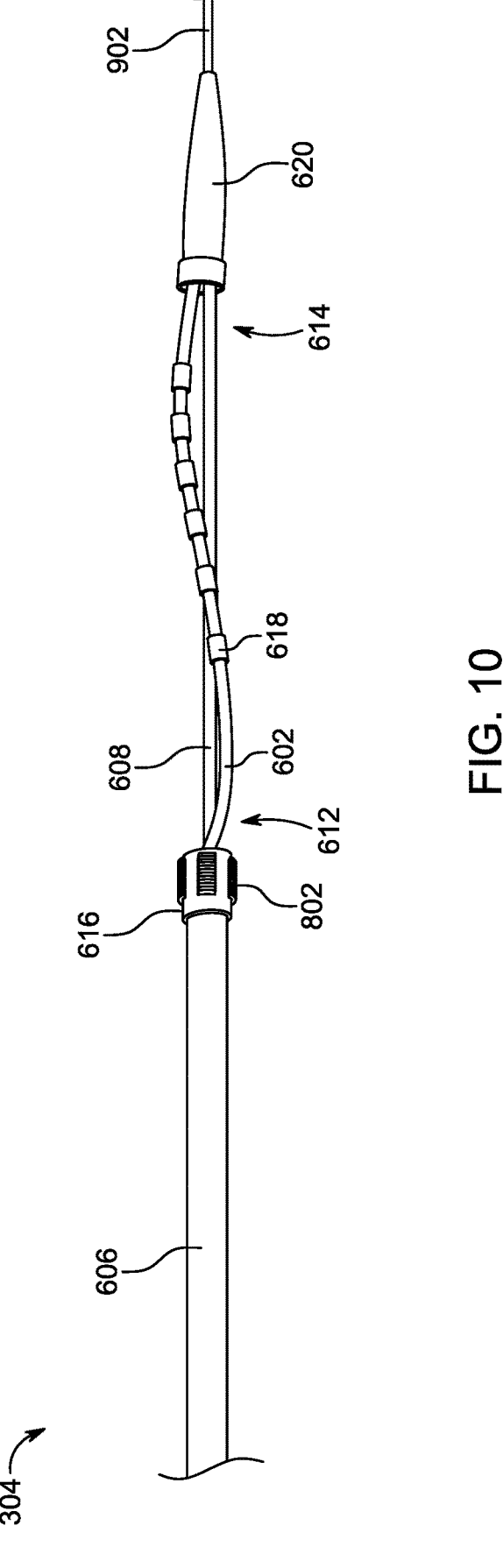
FIG. 10 illustrates a perspective view of a distal portion of the pMUT imaging and mapping catheter in the partially deployed state, with the plurality of linear pMUT imaging arrays arranged in a linear fashion, according to an embodiment of the present disclosure.

In one embodiment, the distal portion of the pMUT imaging and mapping catheter 304 in the partially deployed state, with the plurality of linear pMUT imaging arrays 802 arranged in the linear fashion, as shown in FIG. 10. The plurality of linear pMUT imaging arrays 802 may be arranged over the first ring 616 in the linear fashion.

The present invention provides the pMUT imaging and mapping catheter 304 for performing mapping of targeted tissue on a subject, such as, atrial fibrillation, supra ventricular tachycardia, atrial tachycardia, ventricular tachycardia, ventricular fibrillation, and the like. In one alternate embodiments, the pMUT imaging and mapping catheter 304 may comprise a tubular body member (not shown) having a proximal end and distal end and preferably a lumen extending therebetween. The pMUT imaging and mapping catheter 304 is preferably of the type used for performing intracardiac procedures, typically being per subcutaneously introduced and advanced from the femoral vein in a patient's leg. Alternative methods involve percutaneous introduction into the jugular vein of the patient's neck, or other anatomical entry point that can be used to access the target location within the patient. The pMUT imaging and mapping catheter 304 is preferably introducible through a sheath and preferably is advanceable over a guidewire. The pMUT imaging and mapping catheter 304 preferably has a steerable tip that allows precise positioning of the distal portion.

The pMUT imaging and mapping catheter 304 allow generation of lesions of appropriate size and shape to treat conditions involving disorganized electrical conduction (e.g., atrial fibrillation). The created lesions are segmented and localized. The lesions may be linear or curvilinear, circumferential, and partial circumferential, and/or continuous or discontinuous. The pMUT imaging and mapping catheter 304 are also practical in terms of ease-of-use and limiting risk to the patient, as well as significantly reducing procedure times. The lesions created by the pMUT imaging and mapping catheter 304 are suitable for inhibiting the propagation of inappropriate electrical impulses in the heart for prevention of reentrant arrhythmias.

In one embodiment, energy to the pMUT imaging and mapping catheter 304 may be delivered using pulse width modulated drive signals, well known to those of skill in the art. Further, the energy can also be delivered in a closed loop fashion. Such as a system with temperature feedback wherein the temperature modifies the type, frequency and or magnitude of the energy delivered.

Figure 11:
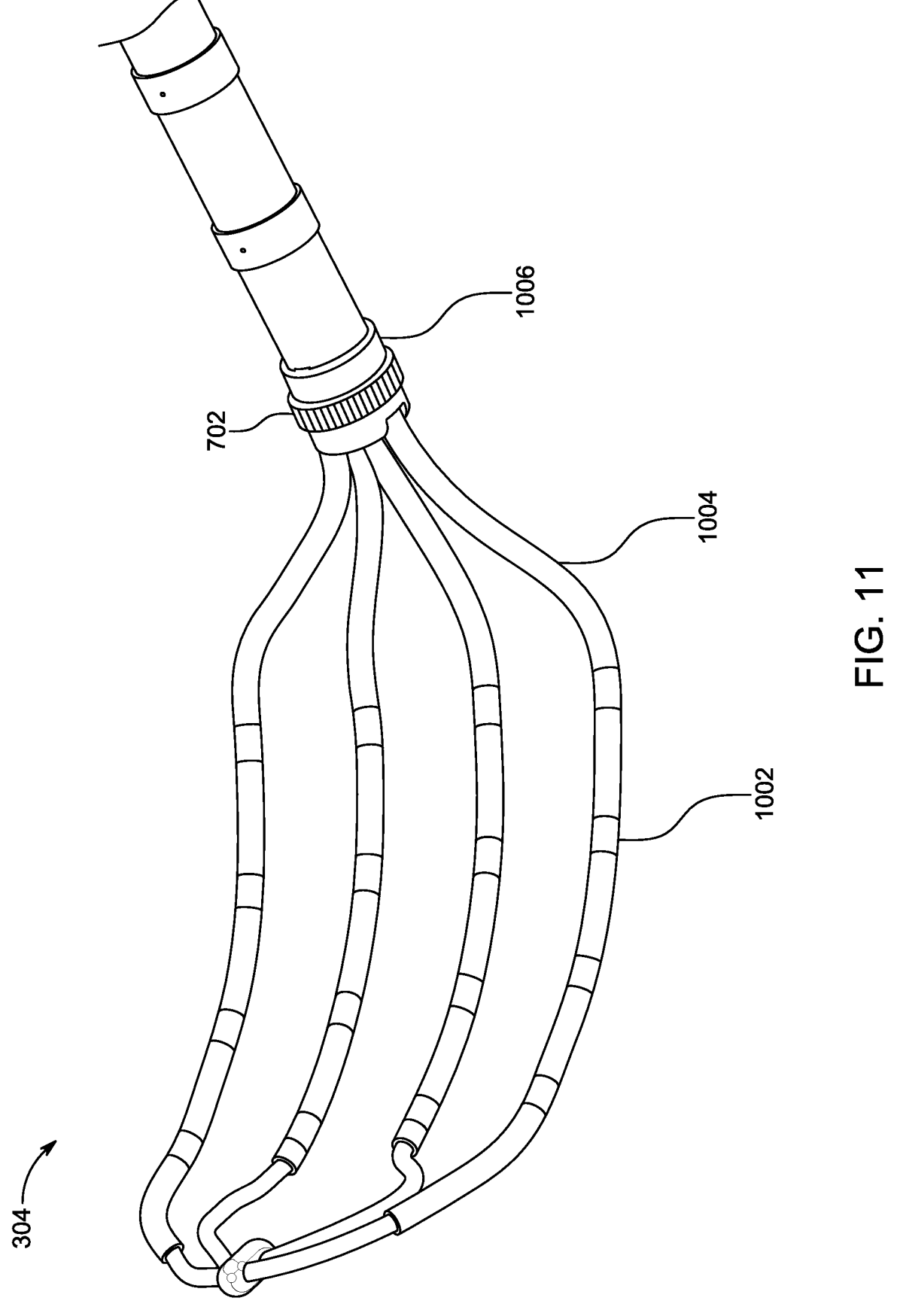
FIG. 11 illustrates a grid mapping view of the pMUT imaging and mapping catheter, with the plurality of circular pMUT imaging arrays arranged in a linear fashion, according to an embodiment of the present disclosure.

Referring to FIG. 11, a grid mapping view of the pMUT imaging and mapping catheter 304, with the plurality of circular pMUT imaging arrays 702 arranged in linear fashion, is disclosed, according to an embodiment of the present disclosure.

Further, the pMUT imaging and mapping catheter 304 may comprise mapping elements 1002 fixedly mounted to each of a plurality of flexible splines 1004. The mapping elements 1002 are configured to map the pathways in the tissue. Further, the mapping elements 1002 are configured to map electrical activity present in tissue to target areas for creating lesions and/or otherwise assess a patient condition. In one embodiment, the mapping elements 1002 are constructed of an electronic sensor, a conductive material, such as platinum or a combination of platinum and iridium. Further, the mapping elements 1002 may comprise integral temperature sensors, such as a thermos couple welded to an internal portion of the mapping elements 1002. In another embodiment, the mapping elements 1002 and integral temperature or other sensors, are attached to wires (not shown) which travel proximally to the proximal portion of the mapping catheter 304 for attachment to an pMUT imaging engine, mapping unit, an energy delivery unit, and/or another electronic device for sending or receiving signals and/or power.

Figure 12:
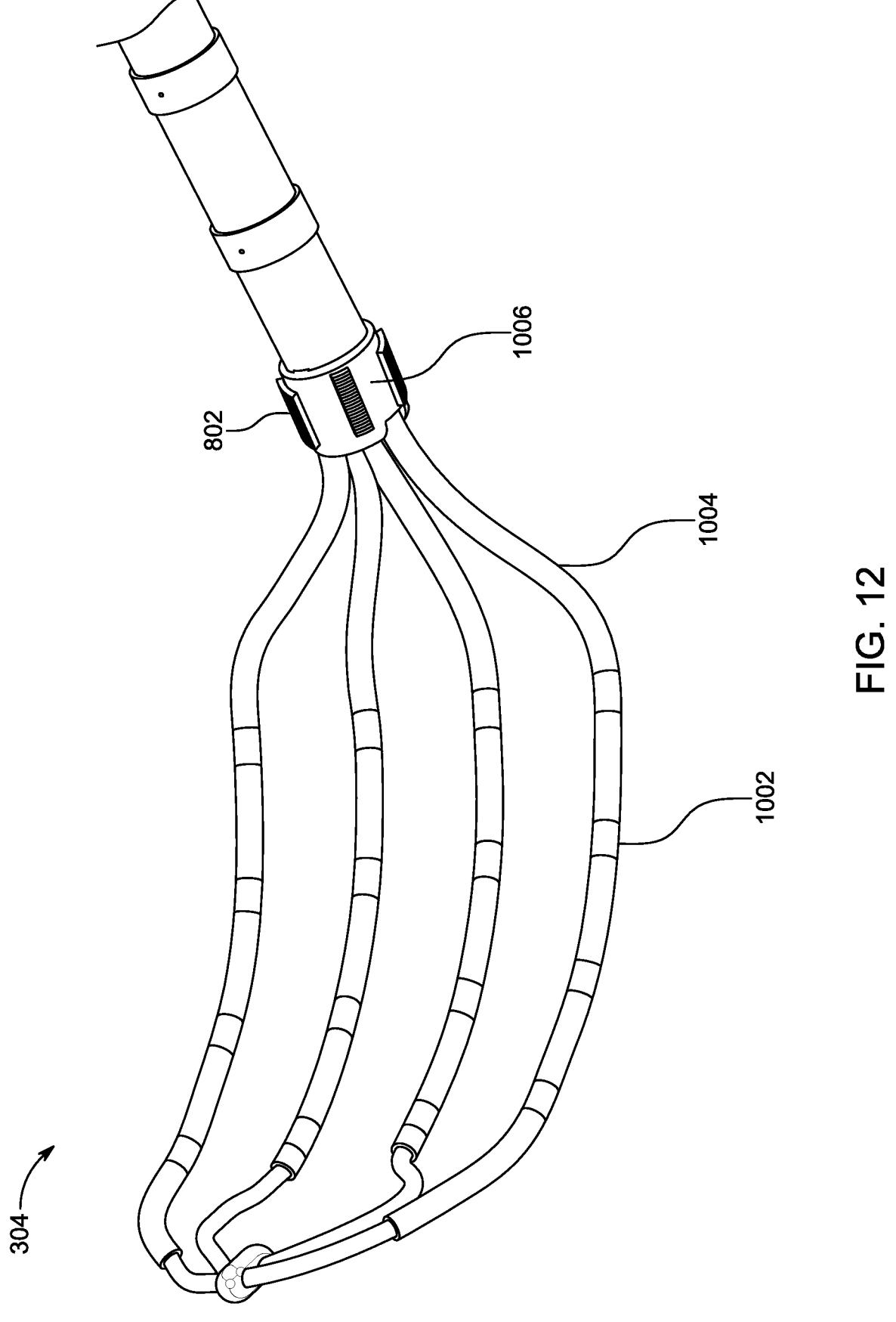
FIG. 12 illustrates a grid mapping view of the pMUT imaging and mapping catheter, with the plurality of linear pMUT imaging arrays arranged in a linear fashion, according to an embodiment of the present disclosure.

Further, the pMUT imaging and mapping catheter 304 may comprise a first ring 1006 having the plurality of circular mapping pMUT arrays 702 arranged in the cylindrical fashion. In one embodiment, the first ring 1006 having the plurality of linear pMUT imaging array 802 arranged in linear fashion, as shown in FIG. 12.

In one embodiment, the plurality of circular mapping pMUT arrays 702 and plurality of linear pMUT imaging array 802 may be arrays of mapping elements, preferably geometrically adjustable electrode arrays, and may be configured in a wide variety of ways and patterns. In another embodiment, the plurality of circular mapping pMUT arrays 702 and plurality of linear pMUT imaging array 802 provide electrical energy, such as radiofrequency (RF) energy, in monopolar (unipolar), bipolar or combined monopolar-bipolar fashion, as well as methods for treating conditions (e.g., atrial fibrillation, supra ventricular tachycardia, atrial tachycardia, ventricular tachycardia, ventricular fibrillation, and the like). Further, multiple types of mapping catheters may be employed for different minimally invasive procedures, such as, atrioventricular (AV) node ablation which is a treatment for an irregularly fast and disorganized heartbeat called atrial fibrillation, cryoablation in which an extremely cold liquid or an instrument called a cryoprobe is used to freeze and eliminate abnormal tissue, and an epicardial ablation in which a regular heart rhythm is restored, by creating tiny scars on outside of the heart to block faulty electrical signals that cause the heart to beat too fast.

In one embodiment, the electrodes or mapping elements may have one or more different shapes. As used herein, the term "proximal and distal energy delivering carrier assemblies" refers to a flexible carrier, on which one or more mapping elements are disposed. The carrier assemblies include one or more carrier arms, as arm segments described above. The carrier assemblies are not limited to, size, or shape, and can be configured to be in expanded and unexpanded or compact states. As used herein, the term "proximal and distal carrier arms" refer to a wire-like shaft capable of interfacing with electrodes and a control shaft. Further, the distal and proximal carrier arms are not limited to any size or measurement.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth here below not be construed as being order-specific unless Such order specificity is expressly stated in the claim.

What is claimed is:

1. An integrated cardiac mapping and piezoelectric micromachined ultrasonic transducer (pMUT) ultrasonic imaging system comprising:

a pMUT imaging and mapping catheter having a longitudinal axis, a proximal end, and a distal end the pMUT imaging and mapping catheter including a catheter shaft that slidably receives a control shaft;

a first micro-electromechanical (MEMS) based pMUT array disposed at the distal end of the pMUT imaging and mapping catheter, wherein the first MEMS based pMUT array comprises a substrate and a plurality of pMUT array elements arranged on the substrate;

a mapping array disposed at the distal end of the pMUT imaging and mapping catheter, wherein the mapping array comprises a plurality of support members with an electronic sensor array arranged on the plurality of support members, wherein a distal end of the plurality of support members is connected to the control shaft and a proximal end of the plurality of support members is connected to the catheter shaft; and a first ring positioned on the control shaft at the proximal end of the plurality of support members, wherein the proximal end of the plurality of support members is directly connected to the first ring and the first ring is configured to attach the proximal end of the plurality of support members to the catheter shaft;

wherein the first MEMS based pMUT array is positioned on the first ring.

2. The integrated cardiac mapping and pMUT ultrasonic imaging system of claim 1, wherein the catheter shaft is connected at one end to a handle assembly and at another end to the first MEMS based pMUT array and the mapping array.

3. The integrated cardiac mapping and pMUT ultrasonic imaging system of claim 1, wherein the pMUT imaging and mapping catheter is coupled to a dongle, and the dongle is configured to communicate ultrasound transmit pulses and ultrasound receive waveforms between the first MEMS based pMUT array and a combined ultrasound and mapping computer system.

4. The integrated cardiac mapping and pMUT ultrasonic imaging system of claim 1, wherein the pMUT imaging and mapping catheter is coupled to a dongle, and the dongle is configured to communicate electronic mapping data between the plurality of support members and a combined ultrasound and mapping computer system.

5. The integrated cardiac mapping and pMUT ultrasonic imaging system of claim 1, wherein each of the plurality of pMUT array elements having transducer cells of multiple diameters, to achieve a wide bandwidth.

6. The integrated cardiac mapping and pMUT ultrasonic imaging system of claim 1, wherein each of the plurality of pMUT array elements is a linear phased array.

7. The integrated cardiac mapping and pMUT ultrasonic imaging system of claim 1, wherein each of the plurality of pMUT array elements is a pMUT circular array.

8. The integrated cardiac mapping and pMUT ultrasonic imaging system of claim 1, wherein the electronic sensor array corresponds to mapping elements.

9. The integrated cardiac mapping and pMUT ultrasonic imaging system of claim 1, wherein the plurality of support members is configured to be placed against an interior wall of a heart.

10. The integrated cardiac mapping and pMUT ultrasonic imaging system of claim 1, further comprising a second ring positioned on the control shaft at the distal end of the plurality of support members, wherein a second MEMS based pMUT array is positioned on the second ring.

11. The integrated cardiac mapping and pMUT ultrasonic imaging system of claim 1, wherein first MEMS based pMUT array is arranged in a linear fashion wherein each of the plurality of pMUT array elements is positioned longitudinally next to another pMUT array element and is oriented perpendicularly to the longitudinal axis of the pMUT imaging and mapping catheter.

* * * * *